(12) United States Patent
Decker et al.

(10) Patent No.: US 8,302,370 B1
(45) Date of Patent: Nov. 6, 2012

(54) PHARMACY PACKAGING AND VALIDATION SYSTEM

(76) Inventors: Timothy Decker, LaVista, NE (US); Brian Monaghan, Omaha, NE (US)

( * ) Notice: Subject to any disclaimer, the term of this patent is extended or adjusted under 35 U.S.C. 154(b) by 243 days.

(21) Appl. No.: 12/784,171

(22) Filed: May 20, 2010

Related U.S. Application Data

(60) Provisional application No. 61/180,248, filed on May 21, 2009.

(51) Int. Cl.
 *B65B 61/00* (2006.01)
(52) U.S. Cl. ............... 53/415; 53/476; 53/473; 53/168
(58) Field of Classification Search .............. 53/415, 53/476, 467, 473, 168, 154, 237, 52
See application file for complete search history.

(56) References Cited

U.S. PATENT DOCUMENTS

| | | | | |
|---|---|---|---|---|
| 5,819,649 A | * | 10/1998 | Townsend et al. | 101/93.01 |
| 5,852,911 A | * | 12/1998 | Yuyama et al. | 53/168 |
| 5,875,610 A | * | 3/1999 | Yuyama et al. | 53/75 |
| 5,905,652 A | * | 5/1999 | Kutsuma | 700/235 |
| 5,964,374 A | * | 10/1999 | Yuyama et al. | 221/17 |

* cited by examiner

*Primary Examiner* — Sameh H. Tawfik
(74) *Attorney, Agent, or Firm* — Advent IP, P.C., L.L.O.

(57) ABSTRACT

A packaging system for pharmaceuticals is provided. The system includes a box having an opening, a pouch strip positioned within the box. The pouch strip includes a continuous series of sealed pouches rolled into a spiral with a first end and a second end. The opening in the box is of a shape configured to accommodate the cross section of the sealed pouches such that the pouch strip may be pulled through the opening outwardly from the box.

8 Claims, 5 Drawing Sheets

PHARMACY PACKAGING AND VALIDATION SYSTEM

CROSS REFERENCE TO RELATED APPLICATION

This application is a non-provisional of U.S. Application Ser. No. 61/180,248 filed on May 21, 2009, which is incorporated by reference herein in its entirety.

BACKGROUND OF THE INVENTION

This invention is related generally to automated pharmaceutical dispensing technology and, more specifically, to an improved method for packaging and validating of pharmacy orders.

Automated dispensing of prescription medications, such as oral solid pills and liquid unit-of use ampules, is a well-known method of filling prescriptions. Dosage-based prescriptions are filled in a way which organizes the medication into one or more dosage units by, for example, the time of day at which the medication is to be taken or the sequence in which the medication is to be taken. Dosage-based automated medication dispensing systems have particular utility in settings where large amounts of such prescription medications are required.

Automated medication dispensing devices typically include one or more computer-controlled dispensing machines which store and dispense medications according to patient-specific prescription information. These advantages include the ability to store a broad range of prescription medications and the ability to fill patient prescriptions in a rapid and efficient manner. In addition, use of automated prescription filling equipment reduces the possibility of human error in filling patient prescriptions. Another advantage is that the cost savings from automated dispensing of medications can be used to employ more pharmacists and care givers who can provide personalized service to patients.

However, such systems have not been utilized in a manner to maximize their potential efficiencies. For example, incorporation of a dosage based system into an overall packaging system would be particularly useful, especially for mail order pharmacies. Additionally, there has been no successful effort to integrate such systems with a semi-automatic prescription validation station that would allow for pharmacist review of each dosage in a streamlined and efficient manner.

BRIEF SUMMARY OF THE INVENTION

Some embodiments relate to A packaging system for pharmaceuticals. The system may include a box having an opening, a pouch strip positioned within the box. The pouch strip includes a continuous series of sealed pouches rolled into a spiral with a first end and a second end. The opening in the box is of a shape configured to accommodate the cross section of the sealed pouches such that the pouch strip may be pulled through the opening outwardly from the box.

Other embodiments relate to a method of packaging a pharmaceutical product. The method includes the steps of dispensing a first pharmaceutical product onto a continuous strip of material, dispensing a second pharmaceutical product onto the continuous strip of material, and forming a first generally flat pouch enclosing an area of the continuous strip of material proximate to the first pharmaceutical product. The first generally flat pouch includes a label on a first side and the first pharmaceutical product is visible through a second side. A second generally flat pouch enclosing art area of the continuous strip of material proximate to the second pharmaceutical product is formed. The second generally flat pouch includes a label on a first side and the second pharmaceutical product is visible through a second side, the first pouch being coupled to the second pouch. An image the label of the first pouch with a first imaging device and an image the first pharmaceutical product through the second side of the first pouch are captured. The first pharmaceutical product shown in the second image is verified to prescription information corresponding to the label on the first pouch. The first pouch is then positioned in a packaging container.

DETAILED DESCRIPTION OF THE INVENTION

Figure 1:
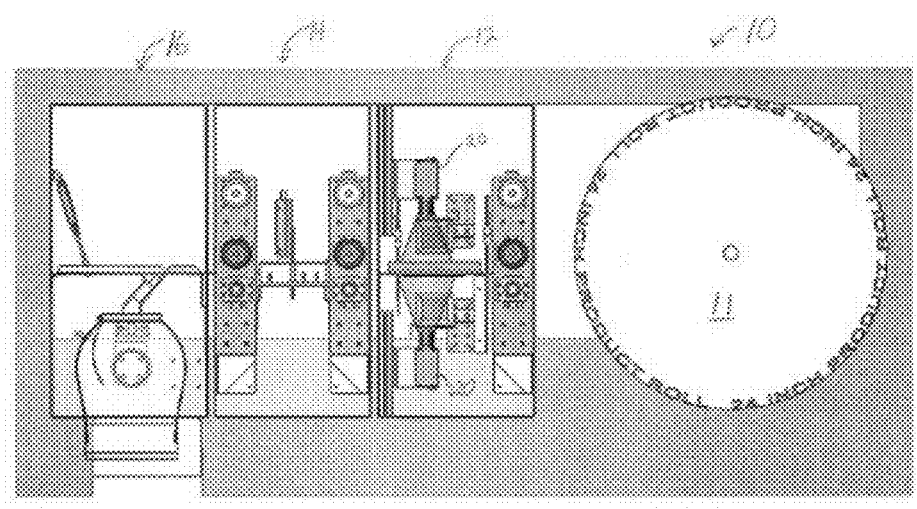
FIG. 1 is a schematic view of a portion of a pharmacy packaging system.

In general, the system includes several stations that each carry out a separate function. The system includes a pre-packaging station, an imaging station, and a winding station. The pre-packaging station may be a prior art station such as a TCGRX ATP Automatic Tablet Packager System available from The Chudy Group LLC. The prepackaging station provides a ship of pouches containing pharmaceutical products according to the methods described in U.S. Pat. No. 6,370,841, the entirety of which is hereby incorporated by reference herein. Pouch strips may then be packaged into cartons. Each carton may correspond to a patient or a facility having multiple patients.

A pouch imaging station may also be provided for pouch image capture and display. Images captured from each of the two color cameras positioned prior to the winder will synchronize front and rear images to allow for Pharmacist verification of each individual pouch packaged into the patient carton. Pharmacist will have the option of accept/reject of each individual patient carton prior to shipment. The station includes a PC workstation, imaging and database software.

Operators may load pre-wound reels (TCGRX APS-100 type) of prepackaged product onto a free-wheeling tensioned axle and thread pouch vine into a set of pinch rollers attached to a pharmacist verification station. The strip passes though the pinch rollers and into the imaging station. The pharmacist imaging station may have two color cameras positioned vertically above and below the strip to image both sides of the pouch and read a barcode, preferably a 2d barcode. The strip engages another set of pinch rollers and enters the cutting station. Here the continuous strip is cut into individual orders between a header and footer pouch of each order. The barcode read at the imaging station may cue the programmable logic controller at which pouch of the strip requires cutting by using the barcode as a fiduciary mark. The strip is tensioned between two sets of pinch rollers and a "guillotine" may be used to separate the pouches at the correct location. The cut strip continues into the servo driven winder and is coiled in preparation to being loaded in a box positioned on the conveyor beneath the winder.

Optionally included is a semi-automatic carton feed and load station. Wound strips will be indexed and automatically fed into an awaiting carton. Included with the system is also the ability to handle different carton sizes. A flat chain conveyor may be used to deliver erected cartons that are loaded by an operator to the winding station. Pneumatic stops and carton sensors may be mounted to the conveyor at the winding station for positioning of the cartons at the proper location during coil insertion.

After the wound strips (i.e. coils) are inserted into the carton, a conveyor will transport the carton to the labeling station (2D barcodes which contains unique order number for the batch may be applied by the pre-packaging station). The operator will present the carton with wound contents to a bar code reader. The order number scanned from the barcode may be used to locate the appropriate patient label file on a network drive. Upon successful reading of the barcode, one of two color printers will print the patient label which includes patient and/or prescription information and a correlating barcode. The carton will be closed by the operator and the label applied. If the bar code verification station rejects the carton for any reason, the carton will be set aside and no label will be printed. An operator can then rotate the coiled strip inside the carton to better position the barcode for a second read then introduce it in front of the scanner for another attempt.

An optional standalone shrinkwrap machine applies wrapping material to a closed product container placed into the machine by the operator. The shrink wrap will apply a postage grade film to the outside of the carton, The carton will be completely wrapped. I of the 6 sides will have transparent film covering the barcode label information. The other 5 sides will be covered with opaque material.

Referring to FIG. 1, system 10 includes a product spool 11 containing a coiled strip of pouches containing one or more pharmaceutical products. The spool may be one such as an APS-100 Spooler available from The Chudy Group LLC. The pouch strip is fed to an imaging station 12 where dual color imagers, shown as cameras 20, image both sides of each pouch. The resulting images are stored in a database. One image captures the pouch label including a 2D barcode, while the other captures an image of the contents of the pouch. The pouch strip is then routed to a cutting station 14, where the strip is cut at a boundary between different orders which are to be packaged separately to provide strip segments. Each segment is then routed to a winding station 16 where each order is wound for separate packaging. The information used to determine the boundary between segments may be tied to the 2D barcode read at the imaging station. System 10 thereby allows for the fully automated imaging and packaging of the pouches.

Figure 2:
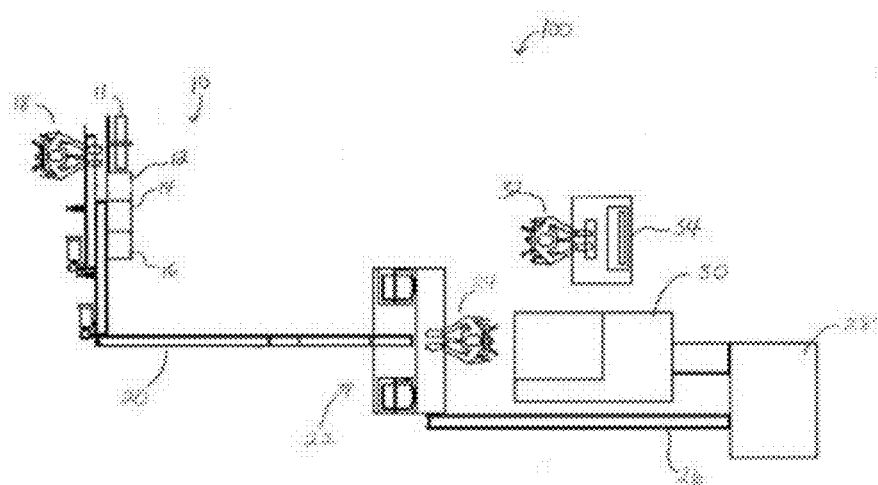
FIG. 2 is a schematic view of a pharmacy packaging system including the portion of FIG. 1.

Referring to FIG. 2, system 10 is incorporated into a larger packaging system 100. System 10 is operated by an operator 18 who is responsible for replacing spools 11 and moving boxed strip segments to conveyor 20. Labeling station 22 is operated by operator 24. As boxed strip segments arrive at labeling station 22 operator 24 verifies the order contained in the box according to the lab& on one of the pouches of the strip segment. This may be done by scanning the 2D barcode on the label. A box label is then printed and applied, either by a machine or by the operator 24. The labeled boxes are then sent along conveyor 26.

The labeled boxes are accumulated on table 28. As a set of boxes accumulates (i.e. boxes destined for the same customer destination) they are passed to shrink wrap station 30 where the set is packaged. Each set may correspond to an individual retail customer, or an institutional customer such as a nursing home. Each box within the set may correspond to an individual patient, or a time of day. In the case of each box corresponding to an individual patient, each pouch may be arranged sequentially such that the patient is administered the pharmaceutical products in each pouch at set times of day. Alternatively, when each box corresponds to a time of day, the packages may sequentially correspond to a different patient within a facility.

Throughout the process, a pharmacist 32 operates the Prescription Validation (PV) Station 34. Pharmacist 32 may be provided with a view of both images provided by the imaging station 12. The pharmacist 32 validates that the contents of the pouch are correct for the corresponding prescription record. The prescription record may be displayed on the label, or alternatively it may be provided as a text obtained from a database based on the 2D barcode on the label.

Figure 3:
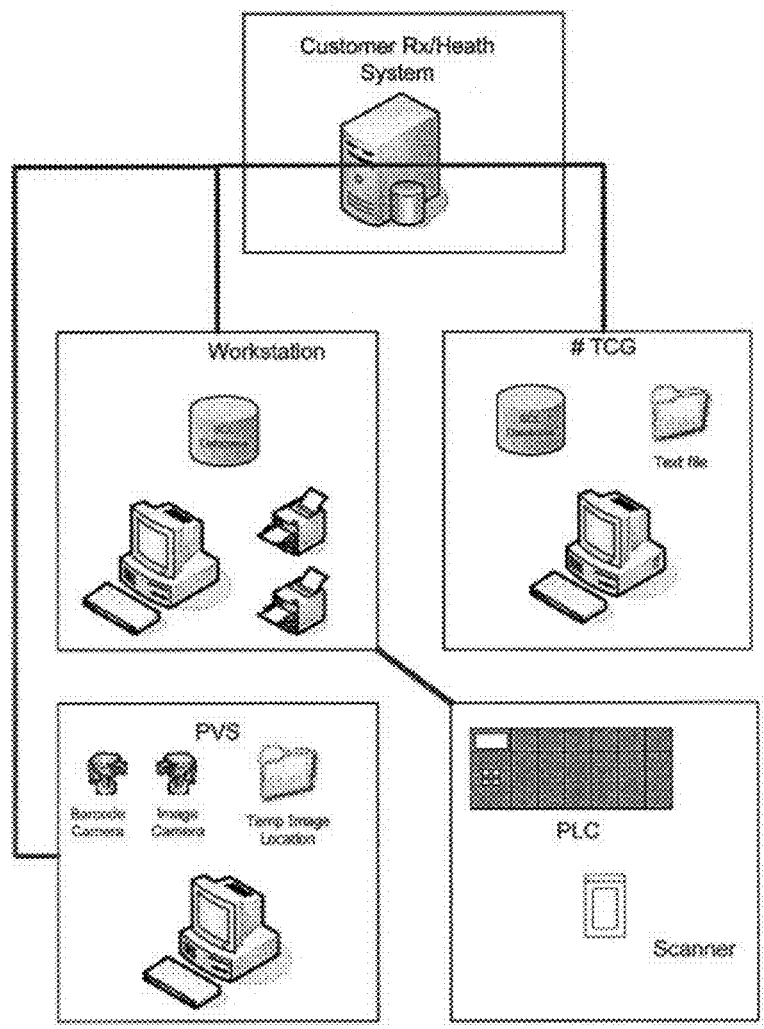
FIG. 3 is a schematic view of a customer prescription health system.

Referring to FIG. 3, a prescription validation system may include a customer prescription health system. An imaging workstation is coupled to a TCG sub system the combination of which includes one or more printers for printing box labels and a database of patient and/or prescription information. The labeling workstation is linked to a programmable logic controller and a scanner for scanning the 2D barcode of a pouch contained in a box to be labeled. When the barcode is scanned it is read and the label is created based on the information in the barcode. A PV system is included to provide images of pouches as described above for validation.

Figure 4:
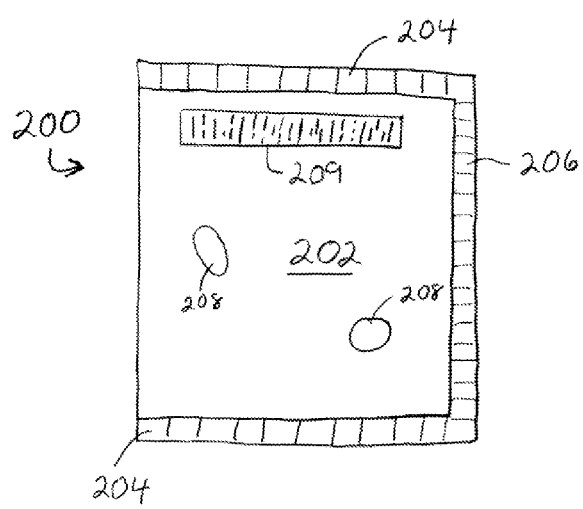
FIG. 4 is an elevation view of a pharmaceutical product pouch.
Figure 5:
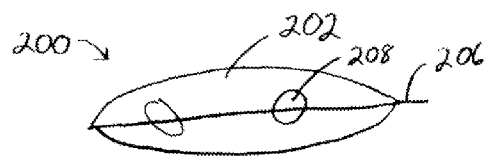
FIG. 5 is a side elevation view of a pharmaceutical product pouch.
Figure 6:
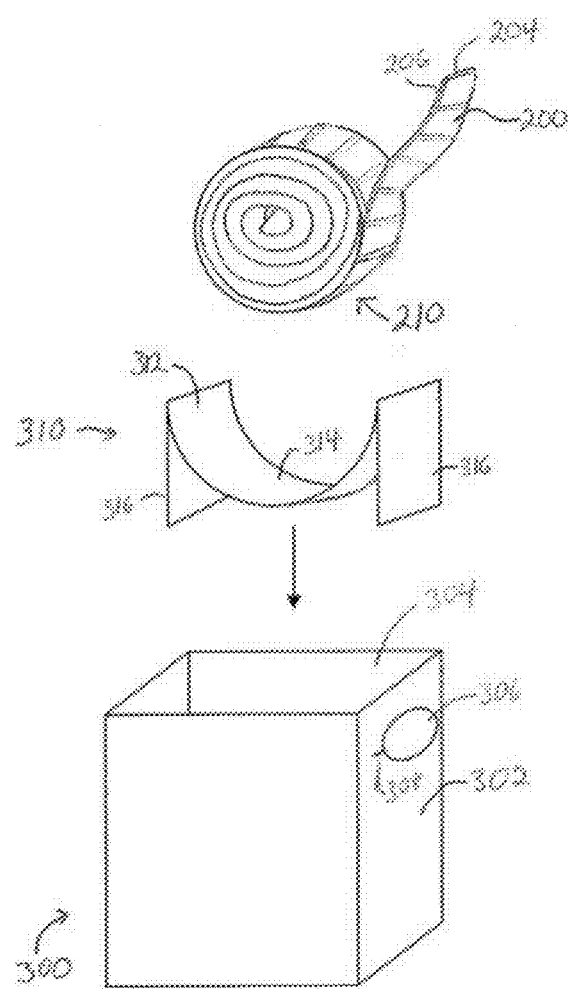
FIG. 6 is an exploded view of a packaging apparatus.

Referring to FIGS. 4, 5, and 6, the pharmaceutical packaging is shown in more detail. A pouch 200 is formed from a folded section of clear plastic. A strip of pouches is created by folding the section laterally and forming sealed edges 204 longitudinally across the strip and sealed edge 206 laterally along the length of the strip. This provides a pouch section 202 for containing pharmaceutical products 208. Label 209 may be affixed to pouch 200. Label 209 may be a 2D label or other suitable label. The produced strip is rolled into a coiled spool 210 for packaging into box 300. Box 300 includes a plurality of sides 302 and a top 304 (shown open). One of sides 302 is provided with an opening 306 that is generally ovular in shape to accommodate the pouches as the are pulled out of box 300 by a patient, facility worker, or other person to remove a pouch of pharmaceutical products. Alternatively, opening 306 may be in the shape of a diamond, rectangle, or other shape. In some embodiments, box 300 may include a cut 308 perpendicular to an edge of opening 406. Cut 308 is configured to receive sealed edge 206 and retain the strip in opening 306, such that the strip does not fall back into box 300. A label provided by labeling station 22 may be affixed to one of the sides 302 or closed top 304 of box 300.

An optional support 310 may be provided. Support 310 may be formed from a continuous piece of cardboard or other material folded to provide legs 316 and a curved cradle 314. When positioned in the box 300, coil 210 may be supported by cradle 314 to prevent coil 210 from flattening under its own weight. If coil 210 flattened it would become very difficult to rotate coil 210 as the strip is pulled through opening 308.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that relative terms are intended to encompass different orientations of the device in addition to the orientation depicted in the Figures.

Moreover, it will be understood that although the terms first and second are used herein to describe various features, elements, regions, layers and/or sections, these features, elements, regions, layers and/or sections should not be limited by these terms. These terms are only used to distinguish one feature, element, region, layer or section from another feature, element, region, layer or section. Thus, a first feature, element, region, layer or section discussed below could be termed a second feature, element, region, layer or section, and similarly, a second without departing from the teachings of the present invention.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Further, as used herein the term "plurality" refers to at least two elements. Additionally, like numbers refer to like elements throughout.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims.

What is claimed is:

1. A method of packaging a pharmaceutical product comprising:
    dispensing a first pharmaceutical product onto a continuous strip of material;
    dispensing a second pharmaceutical product onto the continuous strip of material;
    forming a first generally flat pouch enclosing an area of the continuous strip of material proximate to the first pharmaceutical product, wherein the first generally flat pouch includes a label on a first side and the first pharmaceutical product is visible through a second side;
    forming a second generally flat pouch enclosing an area of the continuous strip of material proximate to the second pharmaceutical product, wherein the second generally flat pouch includes a label on a first side and the second pharmaceutical product is visible through a second side, the first pouch being coupled to the second pouch;
    imaging the label of the first pouch with a first imaging device to produce a first image;
    imaging the first pharmaceutical product through the second side of the first pouch with a second imaging device to produce a second image;
    imaging the label of the second pouch with the first imaging device to produce a third image;
    imaging the second pharmaceutical product through the second side of the second pouch with a second imaging device to produce a fourth image;
    verifying that the first pharmaceutical product shown in the second image corresponds to prescription information corresponding to the label on the first pouch;
    verifying that the second pharmaceutical product shown in the fourth image corresponds to prescription information corresponding to the label on the second pouch; and
    positioning at least one of the first pouch and the second pouch in a packaging container.

2. The method of claim 1, wherein the first pharmaceutical product comprises a one or more prescription medications.

3. The method of claim 1, wherein the step of verifying is carried out by a licensed pharmacist.

4. The method of claim 3, wherein the licensed pharmacist carries out the step of verifying by viewing the first and second images.

5. The method of claim 1, further comprising the step of retrieving a prescription record including prescription information from a database based on information contained in the image of the label of the first pouch.

6. The method of claim 5, wherein the label comprises a barcode and the step of retrieving is conducted based on information included in the barcode.

7. A method of packaging a pharmaceutical product comprising:
    dispensing a first pharmaceutical product onto a continuous strip of material;
    dispensing a second pharmaceutical product onto the continuous strip of material;
    forming a first generally flat pouch enclosing an area of the continuous strip of material proximate to the first pharmaceutical product, wherein the first generally flat pouch includes a label on a first side and the first pharmaceutical product is visible through a second side;
    forming a second generally flat pouch enclosing an area of the continuous strip of material proximate to the second pharmaceutical product, wherein the second generally flat pouch includes a label on a first side and the second pharmaceutical product is visible through a second side, the first pouch being coupled to the second pouch;

imaging the label of the first pouch with a first imaging device to produce a first image;

imaging the first pharmaceutical product through the second side of the first pouch with a second imaging device to produce a second image;

imaging the label of the second pouch with the first imaging device to produce a third image;

imaging the second pharmaceutical product through the second side of the second pouch with a second imaging device to produce a fourth image;

verifying that the first pharmaceutical product shown in the second image corresponds to prescription information corresponding to the label on the first pouch; and verifying that the second pharmaceutical product shown in the fourth image corresponds to prescription information corresponding to the label on the second pouch.

8. The method of claim 7 further comprising the step of coiling a strip comprising the first pouch and the second pouch and placing the curled pouches into a container.

* * * * *